United States Patent [19]

Lesher et al.

[11] 4,265,895

[45] May 5, 1981

[54] 1,2-DIHYDRO-5-PYRIDINYL-3H-PYRAZOLO[3,4-b]PYRIDIN-3-ONES AND THEIR USE AS CARDIOTONICS

[75] Inventors: George Y. Lesher; Monte D. Gruett, both of Schodack, N.Y.

[73] Assignee: Sterling Drug Inc., New York, N.Y.

[21] Appl. No.: 130,623

[22] Filed: Mar. 17, 1980

[51] Int. Cl.³ ............... C07D 471/02; A61K 31/415
[52] U.S. Cl. .................................. 424/256; 546/119; 546/257; 546/258
[58] Field of Search ................... 546/119; 424/256

[56] References Cited

U.S. PATENT DOCUMENTS

| | | | |
|---|---|---|---|
| 3,423,414 | 1/1969 | Blatter | 546/119 |
| 4,004,012 | 1/1977 | Lesher et al. | 546/257 X |
| 4,072,746 | 2/1978 | Lesher et al. | 546/257 X |
| 4,107,315 | 8/1978 | Lesher et al. | 546/257 X |

OTHER PUBLICATIONS

C.A., 87, (1977), 39357t, Balicki, et al.
Balicki et al., Acta Poloniae Pharmaceutica, (1976), vol 33 (3), pp. 289-293.
Nantka–Namirski, et al., Pol. J. Pharmacol. Pharm., (1978), vol. 30, pp. 707-712.

Primary Examiner—Joseph Paul Brust
Attorney, Agent, or Firm—Robert K. Bair; B. Woodrow Wyatt

[57] ABSTRACT

1,2-Dihydro-1-R-5-PY-6-Q-3H-pyrazolo[3,4-b]pyridin-3-ones or pharmaceutically-acceptable acid-addition salts thereof, which are useful as cardiotonic agents, are prepared by reacting lower-alkyl 2-halo-5-PY-6-Q-nicotinate with 1-R-hydrazine. Also disclosed are cardiotonic compositions and method for increasing cardiotonic contractility using said compounds or salts.

13 Claims, No Drawings

1,2-DIHYDRO-5-PYRIDINYL-3H-PYRAZOLO[3,4-B]PYRIDIN-3-ONES AND THEIR USE AS CARDIOTONICS

CROSS-REFERENCE TO RELATED APPLICATION

Copending U.S. patent application Ser. No. 130,628, filed Mar. 17, 1980, discloses and claims the use of lower-alkyl 2-halo-5-(pyridinyl)nicotinates in cardiotonic compositions and method for increasing cardiac contractility. Said lower-alkyl 2-halo-5-(pyridinyl)nicotinates are disclosed herein as intermediates for preparing 1,2-dihydro-1-substituted-5-(pyridinyl)-3H-pyrazolo[3,4-b]pyridin-3-ones, which are useful as cardiotonic agents.

BACKGROUND OF THE INVENTION (a) Field of the Invention

This invention relates to pyrazolo[3,4-b]pyridin-3-ones, their preparation and their use as cardiotonics.

(b) Description of the Prior Art

Chemical Abstracts, Vol. 87, item 39,357t, 1977, reads as follows:

"Dipyridyls. VII. Reaction of β-ketoaldehydes with cyanoacetic acid hydrazide. Balicki, Roman; Kaczmarek, Lukasz; Nantka-Namirski, Pawel (Inst. Org. Chem., Pol. Acad. Sci., Warsaw, Pol.). Acta Pol. Pharm. 1976, 33(3), 289–93 (Pol). RCOCH$_2$CHO (R=Me, Ph, 3- and 4-pyridyl, and

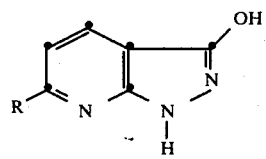

6-methyl-3-pyridyl) condensed in an alk. medium with NCCH$_2$=CONHNH$_2$ (I) to give the pyrazolopyridines II. II were also obtained when 5-amino-3-pyrazolone was used instead of I. II (R=3- and 4-pyridyl) were also prepd. in the reaction of Me 6-(3- and 4-pyridyl)-2-chloronicotinates or 6-(3- and 4-pyridyl)-2-chloro-3-cyanopyridines with 80% NH$_2$NH$_2$.H$_2$O."

The original article (p. 291) shows that the compounds of formula II (supra) can also exist in tautomeric 1,2-dihydro-6-R-3H-pyrazolo[3,4-b]pyridin-3-one form.

In a later paper entitled, "Cancerstatics III. Synthesis and Some Chemical Transformations of 3-Cyano-5-(pyridinyl-4)pyrid-2-one" [Pol. J. Pharmacol. Pharm. 30, 707–712 (1978)], P. Nantka-Namirski and L. Kaczmarek show, inter alia, the reaction of 3-cyano-5-(4-pyridinyl)pyrid-2-one [alternatively named 1,2-dihydro-2-oxo-5-(4-pyridinyl)nicotinonitrile] with phosphorus oxychloride to prepare 2-chloro-3-cyano-5-(4-pyridinyl)pyridine [alternatively named 2-chloro-5-(4-pyridinyl)nicotinonitrile] and the acid hydrolysis of the 3-cyano compound to the corresponding 3-carboxylic acid.

SUMMARY OF THE INVENTION

In a composition of matter aspect, the invention relates to 1,2-dihydro-1-R-5-PY-6-Q-3H-pyrazolo[3,4-b]pyridin-3-ones, where R$_1$ PY and Q are defined herein below or pharmaceutically-acceptable acid-addition salt thereof which are useful as cardiotonic agents.

The invention in a process aspect comprises reacting lower-alkyl 2-halo-5-PY-6-Q-nicotinate with 1-R-hydrazine to produce 1,2-dihydro-R-5-PY-6-Q-3H-pyrazolo[3,4-b]pyridin-3-one.

A composition aspect of the invention relates to a cardiotonic composition for increasing contractility in a patient, said composition comprising a pharmaceutically-acceptable carrier and, as the active ingredient thereof, an effective amount of a cardiotonic 1,2-dihydro-1-R-5-PY-6-Q-3H-pyrazolo[3,4-b]pyridin-3-one or pharmaceutically-acceptable acid-addition salt thereof.

In a method aspect, the invention relates to a method for increasing cardiac contractility in a patient requiring such treatment which comprises the administration of a medicament comprising a pharmaceutically-acceptable carrier and, as the active component, thereof, an effective amount of the cardiotonic 1-R-5-PY-6-Q-3H-pyrazolo[3,4-b]pyridin-3-one or pharmaceutically-acceptable acid-addition salt thereof.

DETAILED DESCRIPTION INCLUSIVE OF PREFERRED EMBODIMENTS

In a composition of matter aspect the invention resides in 1,2-dihydro-1-R-5-PY-6-Q-3H-pyrazolo[3,4-b]pyridin-3-one having formula I

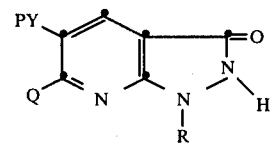

where R is lower-alkyl, lower-hydroxyalkyl, 2,3-dihydroxypropyl or lower-alkoxyalkyl, Q is hydrogen or lower-alkyl, and PY is 4- or 3-pyridinyl or 4- or 3-pyridinyl having one or two lower-alkyl substituents, or pharmaceutically-acceptable acid-addition salts thereof. These compounds are useful as cardiotonic agents, as determined by standard pharmacological evaluation procedures. Preferred embodiments are those of formula I where PY is 4-pyridinyl or 3-pyridinyl, R is methyl, ethyl or 2-hydroxyethyl and Q is hydrogen, methyl or ethyl.

The compound of formula I may exist in tautomeric forms, that is, as the 1,2-dihydro-1-R-5-PY-6-Q-3H-pyrazolo[3,4-b]pyridin-3-one of formula I and/or 1-R-5-PY-6-Q-1H-pyrazolo[3,4-b]pyridin-3-ol of formula IA, illustrated as follows:

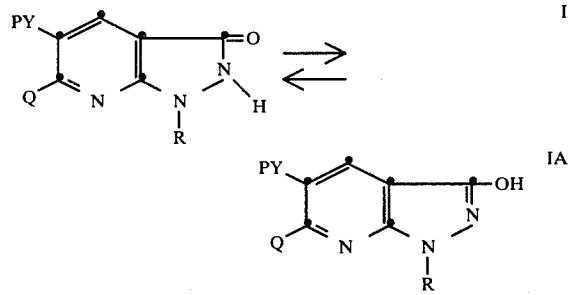

Structural preferences for analogous known pyrazolo[3,4-b]pyridin-3-ones would indicate the above formula I to be the preferred tautomeric structure; thus, it is preferred to use the names based on structure I, although it is understood that either or both structures are comprehended herein.

In a process aspect the invention resides in the process of producing the 1,2-dihydro-1-R-5-PY-6-Q-3H-pyrazolo[3,4-b]pyridin-3-one of formula I which comprises reacting lower-alkyl 2-halo-5-PY-6-Q-nicotinate (II) with 1-R-hydrazine (III), where PY, R and Q have the meanings given above for the compound of formula I and halo is chloro or bromo. Preferred embodiments of this process are those which produce the above-said preferred composition embodiments of formula I and halo is chloro.

Composition aspect of the invention resides in a cardiotonic composition for increasing cardiac contractility, said composition comprising a pharmaceutically-acceptable carrier and, as the active component thereof, an effective amount of a cardiotonic 1,2-dihydro-1-R-5-PY-6-Q-3H-pyrazolo[3,4-b]pyridin-3-one of formula I, where R, PY and Q are each defined as in formula I, or pharmaceutically-acceptable acid-addition salt thereof. Preferred embodiments are those having as active components the above-said preferred embodiments of formula I.

A method aspect of the invention resides in the method for increasing cardiac contractility in a patient requiring such treatment which comprises administering orally or parenterally in a solid or liquid dosage form to such patient an effective amount of a cardiotonic 1,2-dihydro-1-R-5-PY-6-Q-3H-pyrazolo[3,4-b]pyridin-3-one of formula I where PY, R and Q are defined as in formula I, or pharmaceutically-acceptable acid-addition salt thereof. Preferred embodiments of this method aspect are those using the preferred cardiotonics of formula I noted above.

The term "lower-alkyl" as used herein, e.g., as the meaning for R or Q or as a substituent for PY in formula I or as the lower-alkyl moiety of the intermediate lower-alkyl 2-halo-5-PY-6-Q-nicotinate (II), means alkyl radicals having from 1 to 6 carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

Illustrative of PY in formula I where PY is 4-, 3- or 2-pyridinyl having 1 or 2 lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The term "lower-hydroxyalkyl" as used herein, e.g., for one of the meanings for R in formula I, means hydroxy-alkyl radicals having from two to six carbon atoms which can be arranged as straight or branched chains and at least two carbon atoms of which separate hydroxy and the 1-ring nitrogen atom of the pyrazolo[3,4-b]pyridine ring, illustrated by 2-hydroxyethyl, 3-hydroxypropyl, 2-hydroxypropyl, 4-hydroxybutyl, 3-hydroxybutyl, 5-hydroxyamyl, 6-hydroxyhexyl, and the like.

The term "lower-alkoxyalkyl" as used herein, e.g., for one of the meanings for R in formula I, means alkoxyalkyl radicals having from three to six carbon atoms which can be arranged as straight or branched chains and at least two carbon atoms of which separate the oxygen atom of alkoxyalkyl and the 1-ring nitrogen atom of the pyrazolo[3,4-b]pyridine ring, illustrated by 2-methoxyethyl, 2-ethoxyethyl, 3-methoxypropyl, 2-methoxypropyl, 2-methoxybutyl, 4-ethoxybutyl, 3-ethoxypropyl, 3-n-propoxypropyl, and the like.

The compounds of formula I are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base (I) are not vitiated by side effects ascribable to the anions. In practicing the invention, it is convenient to use the free base form; however, appropriate pharmaceutically-acceptable salts within the scope of the invention are those derived from mineral acids such as hydrochloric acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartrate, methanesulfonate, ethanesulfonate, benzenesulfonate, cyclohexylsulfamate and quinate, respectively.

The acid-addition salts of said basic compound (I) are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound (I) are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically-acceptable salt by ion exchange procedures.

The molecular structure of the compound of formula I was assigned on the basis of evidence provided by infrared, nuclear magnetic resonance and mass spectra, and by the correspondence of calculated and found values for the elementary analysis.

The manner of making and using the instant invention will now be generally described so as to enable a person skilled in the art of pharmaceutical chemistry to make and use the same, as follows.

The preparation of 1,2-dihydro-1-R-5-PY-6-Q-3H-pyrazolo-[3,4-b]pyridin-3-one (I) by reacting lower-alkyl 2-halo-5-PY-6-Q-nicotinate (II) with 1-R-hydrazine (III) is carried out by heating the reactants in a suitable solvent at about 50° C. to 100° C., preferably about 65° C. to 85° C. The reaction is conveniently run by refluxing the reactants in a lower-alkanol, preferably methanol or ethanol.

The lower-alkyl 2-halo-5-PY-6-Q-nicotinate is readily prepared by reacting 1,2-dihydro-2-oxo-5-PY-6-Q-nicotinic acid with excess phosphorus oxychloride, preferably with a catalytic amount of dimethylformamide, to produce 2-chloro-5-PY-6-Q'-nicotinoyl chloride and reacting the latter with a lower-alkanol. The reaction is conveniently run by heating the reactants on a steam bath. Other suitable solvents include acetonitrile, dioxane, and the like. Other suitable halogenating agents include $PCl_3$, $PBr_3$, $PCl_5$, and the like.

The preparation of the known 1,2-dihydro-2-oxo-5-PY-nicotinic acids by hydrolysis of the corresponding 1,2-dihydro-2-oxo-5-PY-nicotinonitrile is shown in Lesher and Opalka U.S. Pat. No. 4,004,012, issued Jan. 18, 1977.

The hydrolysis of 1,2-dihydro-6-(lower-alkyl)-2-oxo-5-PY-nicotinonitrile to produce 1,2-dihydro-6-(lower-alkyl)-2-oxo-5-PY-nicotinic acid is conveniently run by heating the nitrile on a steam bath with an aqueous mineral acid, e.g., 50% sulfuric acid, as further illustrated below in Examples E-1 through E-11.

The preparation of the intermediate 1,2-dihydro-2-oxo-5-PY-6-(lower-alkyl)-nicotinonitriles are prepared by the procedure described in the following three paragraphs; this subject matter is disclosed and claimed in copending U.S. patent application Ser. No. 92,504, filed Nov. 26, 1979.

The preparation of 1-PY-2-(dimethylamino)ethenyl lower-alkyl ketone by reacting PY-methyl lower-alkyl ketone with dimethylformamide di-(lower-alkyl) acetal is carried out by mixing the reactants in the presence or absence of a suitable solvent. The reaction is conveniently run at room temperature, i.e., about 20°–25° C., or by warming the reactants up to about 100° C., preferably in an aprotic solvent, conveniently hexamethylphosphoramide because of the method used to prepare the PY-methyl lower-alkyl ketone, as noted below in Example C-1. Other suitable solvents include tetrahydrofuran, dimethylformamide, acetonitrile, ether, benzene, dioxane, and the like. Also, the reaction can be run using no solvent, preferably using an excess of dimethylformamide di-(lower-alkyl)acetal.

The intermediate PY-methyl lower-alkyl ketones are generally known compounds which are prepared by known methods [e.g., as given in Rec. trav. chim 72, 522 (1953); U.S. Pat. No. 3,133,077 (May 12, 1964); Bull. Soc. Chim. France 1968, 4132; Chem. Abstrs. 79, 8539h (1973); Chem. Abstrs. 81, 120,401a (1974); J. Org. Chem. 39, 3834 (1974); Chem. Abstrs. 87, 6594q (1977); J. Org. Chem. 43 2286 (1978)].

The reaction of 1-PY-2-(dimethylamino)ethenyl lower-alkyl ketone with α-cyanoacetamide to produce 1,2-dihydro-2-oxo-5-PY-6-R-nicotinonitrile is carried out preferably by heating the reactants in a suitable solvent in the presence of a basic condensing agent. The reaction is conveniently run using an alkali lower-alkoxide, preferably sodium methoxide or ethoxide, in dimethylformamide. In practicing the invention, the reaction was carried out in refluxing dimethylformamide using sodium methoxide. Alternatively, methanol and sodium methoxide or ethanol and sodium ethoxide can be used as solvent and basic condensing agent, respectively; however, a longer basic period is required. Other basic condensing agents and solvents include sodium hydride, lithium diethylamide, lithium diisopropylamide, and the like, in an aprotic solvent, e.g., tetrahydrofuran, acetonitrile, ether, benzene, dioxane, and the like.

The subject matter of the last three paragraphs is further illustrated in Examples C-1 through C-11 and D-1 through D-11.

The following examples will further illustrate the invention without, however, limiting it thereto.

A. Lower-alkyl 2-Halo-5-PY-6-Q-nicotinates

A-1. Methyl 2-Chloro-5-(4-pyridinyl)nicotinate—A suspension containing 54 g. of 1,2-dihydro-2-oxo-5-(4-pyridinyl)nicotinic acid, 500 ml. of phosphorous oxychloride and 10 drops of dimethylformamide was heated on a steam bath for 4½ hours during which time hydrogen chloride was evolved and most of the solid dissolved. The reaction mixture was allowed to stand overnight at room temperature and was then filtered through diatomaceous earth to remove a small quantity of yellow solid. The excess phosphorus oxychloride in the filtrate was distilled off in vacuo and the syrupy residue was cooled. To this material was added 500 ml. of absolute methanol and the mixture was shaken well with periodic cooling in an ice bath, whereupon the syrup slowly dissolved and a nearly white solid formed. The mixture was cooled well in an ice bath and the solid was collected and air dried. The resulting solid (44.7 g., m.p. 295°–300° C. with decomposition) was taken up in about 500 ml. of water and the solution filtered. The filtrate was basified to pH 8.0 with 3 N ammonium hydroxide solution (about 70 ml. required). The copious pale yellow solid was collected, washed with water and air-dried. The solid was then taken up in 400 ml. of methylene dichloride whereupon a small water layer separated. The methylene dichloride layer was separated, washed with water, dried over an anhydrous magnesium sulfate and then evaporated to dryness on a rotary vaporizer to yield 35.6 g. of a cream-colored solid, m.p. 110°–112° C. A portion of this product, methyl 2-chloro-5-(4-pyridinyl)nicotinate, was recrystallized from 50 ml. of acetonitrile, air-dried and then dried in a vacuum oven at 60° C. for 6 hours to yield 6.7 g. of the product, m.p. 112.5°–113° C.

Following the procedure described in Example A-1 but using in place of 1,2-dihydro-2-oxo-5-(4-pyridinyl)-nicotinic acid and methanol molar equivalent quantities of the appropriate 1,2-dihydro-2-oxo-5-PY-nicotinic acid and lower-alkanol, respectively, it is contemplated that the corresponding lower-alkyl 2-chloro-5-PY-nicotinoates of Examples A-2 through A-7 can be obtained.

A-2. Ethyl 2-chloro-5-(3-pyridinyl)nicotinate.

A-3. n-Propyl 2-chloro-5-(2-methyl-3-pyridinyl)-nicotinate.

A-4. Isopropyl 2-chloro-5-(5-methyl-3-pyridinyl)-nicotinate.

A-5. n-Butyl 2-chloro-5-(3-ethyl-4-pyridinyl)-nicotinate.

A-6. n-Hexyl 2-chloro-5-(2-methyl-4-pyridinyl)-nicotinate.

A-7. Methyl 2-chloro-5-(2,6-dimethyl-4-pyridinyl)-nicotinate.

Following the procedure described in Example A-1 but using in place of phosphorus oxychloride or lower-alkanol molar equivalent quantities of the appropriate halogenating agent and lower-alkanol, respectively, it is contemplated that the designated lower-alkyl 2-halo-5-(4-pyridinyl)nicotinate of Examples A-8 or A-9 can be obtained.

A-8. Methyl 2-bromo-5-(4-pyridinyl)nicotinate using phosphorus tribromide or phosphorus oxybromide and absolute methanol.

A-9. Ethyl 2-chloro-5-(4-pyridinyl)nicotinate using phosphorus trichloride, phosphorus pentachloride or sulfuryl chloride and absolute ethanol.

Following the procedure described in Example A-1 but using in place of 1,2-dihydro-2-oxo-5-(4-pyridinyl)-nicotinic acid a molar equivalent quantity of the appropriate 1,2-dihydro-2-oxo-5-PY-6-(lower-alkyl)nicotinic acid and either methanol or a molar equivalent quantity of the appropriate lower-alkanol, it is contemplated that the corresponding lower-alkyl 2-chloro-5-PY-6-(lower-alkyl)nicotinates of Examples A-10 through A-20 can be obtained.

A-10. Methyl 2-chloro-6-methyl-5-(4-pyridinyl)-nicotinate.

A-11. Ethyl 2-chloro-6-ethyl-5-(4-pyridinyl)-nicotinate.

A-12. Methyl 2-chloro-6-methyl-5-(3-pyridinyl)-nicotinate.

A-13. Methyl 2-chloro-6-n-propyl-5-(4-pyridinyl)-nicotinate.

A-14. Ethyl 2-chloro-6-isopropyl-5-(4-pyridinyl)-nicotinate.

A-15. Methyl 6-n-butyl-2-chloro-5-(4-pyridinyl)-nicotinate.

A-16. Methyl 2-chloro-6-isobutyl-5-(4-pyridinyl)-nicotinate.

A-17. Ethyl 2-chloro-5-(4-pyridinyl)-6-tert.-butyl-nicotinate.

A-18. Methyl 2-chloro-6-n-pentyl-5-(4-pyridinyl)-nicotinate.

A-19. n-Butyl 2-chloro-6-ethyl-5-(2-methyl)-4-pyridinyl)nicotinate.

A-20. Isopropyl 2-chloro-6-ethyl-5-(3-pyridinyl)-nicotinate.

B.
1,2-Dihydro-5-(pyridinyl)-3H-pyrazolo[3,4-b]pyridin-3-ones

B-1. 1,2-Dihydro-1-methyl-5-(4-pyridinyl)-3H-pyrazolo[3,4-b]pyridin-3-one—A solution containing 4.2 g. of methyl 2-chloro-5-(4-pyridinyl)nicotinate, 5 ml of 1,1-dimethylhydrazine and 50 ml. of methanol was refluxed with stirring for 20 hours the reaction mixture was then cooled, the solid collected, washed with ethanol and dried at 90° C. to produce 1.7 g. of 1,2-dihydro-1-methyl-5-(4-pyridinyl)-3H-pyrazolo[3,4b]pyridine-3-one. This 1.7 g. of 1,2-dihydro-1-methyl-5-(4-pyridinyl)-3H-pyrazolo[3,4-b]pyridine-3-one was combined with 4.3 g. and 1.4 g. portions of corresponding product obtained from two other runs and the combined product was recrystallized from 30 ml. of dimethylformamide and dried in a vacuum oven at 90° C. yield 4.7 g. of 1,2-dihydro-1-methyl-5-(4-pyridinyl)-3H-pyrazolo[3,4-b]pyridine-3-one, m.p. 265°–267° C.

The above preparation was preferably run using 1-methylhydrazine instead of 1,1-dimethylhydrazine, as follows: To a stirred warm solution of 5.0 g. of methyl 2-chloro-5-(4-pyridinyl)nicotinate in 40 ml. of methanol was added 5 ml. of 1-methylhydrazine and the resulting reaction mixture was refluxed with stirring for eighteen hours. The reaction mixture containing a small amount of solid was cooled. Since only little additional solid separated, the solvent was removed using a rotary evaporator. The remaining yellow solid was collected, washed with water and dried in a vacuum oven at 90° C. to yield 4.3 g. of 1,2-dihydro-1-methyl-5-(4-pyridinyl-3H-pyrazolo[3,4-b]pyridin-3-one, m.p. 263°–265° C.

For purpose of comparison, the following compound, which differs structurally from Example B-1 in having no 1-substituent (other than hydrogen) where Example B-1 has methyl, was prepared by the following procedure: a solution containing 16.6 g. of methyl 2-chloro-5-(4-pyridinyl)nicotinoate, 19 ml. of hydrazine hydrate and 150 ml. of methanol was refluxed on a steam bath for 19 hours and the mixture containing a yellow solid was cooled well in ice and the solid collected. The solid was air-dried, 11.2 g., and combined with a 1.6 g. portion of corresponding product obtained in another run following the same procedure and the combined product was recrystallized from 440 ml. of dimethylformamide, washed with ether and dried in a vacuum oven at 95° C. to yield 9.5 g. of 1,2-dihydro-5-(4-pyridinyl)-3H-pyrazolo[3,4-b]pyridin-3-one, m.p. >300° C. In contrast to the cardiotonically-active Example B-1, this 1-unsubstituted compound was found to be inactive when tested in the in vitro cardiotonic cat atria screen as shown hereinbelow.

Following the procedure described in Example B-1 but using in place of 1,1-dimethylhydrazine or 1-methylhydrazine a molar equivalent quantity the appropriate 1-R-hydrazine, it is contemplated that the corresponding 1,2-dihydro-1-R-(4-pyridinyl)3H-pyrazolo[3,4-b]pyridin-3-ones of Examples B-2 through B-13 can be obtained.

B-2. 1,2-Dihydro-1-(2-methoxypropyl)-5-(4-pyridinyl)-3H-pyrazolo[3,4-b]pyridin-3-one.

B-3. 1,2-Dihydro-1-ethyl-5-(4-pyridinyl)-3H-pyrazolo[3,4-b]pyridin-3-one using 1-ethylhydrazine.

B-4. 1,2-Dihydro-1-n-propyl-5-(4-pyridinyl)-3H-pyrazolo[3,4-b]pyridin-3-one using 1-n-propylhydrazine.

B-5. 1,2-Dihydro-1-isopropyl-5-(4-pyridinyl)-3H-pyrazolo[3,4-b]pyridin-3-one using 1-isopropylhydrazine.

B-6. 1,2-Dihydro-1-n-butyl-5-(4-pyridinyl)-3H-pyrazolo[3,4-b]pyridin-3-one using 1-n-butylhydrazine.

B-7. 1,2-Dihydro-1-isobutyl-5-(4-pyridinyl)-3H-pyrazolo[3,4-b]pyridin-3-one using 1-isobutylhydrazine.

B-8. 1,2-Dihydro-1-(2-butyl)-5-(4-pyridinyl)-3H-pyrazolo[3,4-b]pyridin-3-one using 1-(2-butyl)hydrazine.

B-9. 1,2-Dihydro-1-(n-amyl)-5-(4-pyridinyl)-3H-pyrazolo[3,4-b]pyridin-3-one using 1-(n-amyl)hydrazine.

B-10. 1,2-Dihydro-1-(n-hexyl)-5-(4-pyridinyl)-3H-pyrazolo[3,4-b]pyridin-3-one using 1-(n-hexyl)hydrazine.

B-11. 1,2-Dihydro-1-(2-ethoxyethyl)-5-(4-pyridinyl)-3H-pyrazolo[3,4-b]pyridin-3-one using 1-(2-ethoxyethyl)hydrazine.

B-12. 1,2-Dihydro-1-(2-methoxyethyl)-5-(4-pyridinyl)-3H-pyrazolo[3,4-b]pyridin-3-one using 1-(2-methoxyethyl)hydrazine.

B-13. 1,2-Dihydro-1-(3-methoxypropyl)-5-(4-pyridinyl)-3H-pyrazolo[3,4-b]pyridin-3-one using 1-(3-methoxypropyl)hydrazine.

Following the procedure in Example B-1 but using in place of methyl 2-chloro-5-(4-pyridinyl)nicotinate and 1,1-dimethylhydrazine or 1-methylhydrazine respectively, corresponding molar equivalent quantities of the respective appropriate methyl or other lower-alkyl 2-chloro-5-PY-nicotinate and 1-R-hydrazine, it is contemplated that there can be obtained the corresponding 1,2-dihydro-1-R-5-PY-3H-pyrazolo[3,4-b]pyridin-3-ones of Examples B-14 through B-19.

B-14. 1,2-Dihydro-1-methyl-5-(3-pyridinyl)-3H-pyrazolo[3,4-b]pyridin-3-one.

B-15. 1,2-Dihydro-5-(2-methyl-3-pyridinyl)-3H-pyrazolo[3,4-b]pyridin-3-one.

B-16. 1,2-Dihydro-1-ethyl-5-(5-methyl-3-pyridinyl)-3H-pyrazolo[3,4-b]pyridin-3-one.

B-17. 1,2-Dihydro-1-methyl-5-(3-ethyl-4-pyridinyl)-3H-pyrazolo[3,4-b]pyridin-3-one.

B-18. 1,2-Dihydro-1-(2-methoxyethyl)-5-(2-methyl-4-pyridinyl)-3H-pyrazolo[3,4-b]pyridin-3-one.

B-19. 1,2-Dihydro-1-methyl-5-(2,6-dimethyl-4-pyridinyl)-3H-pyrazolo[3,4-b]pyridin-3-one.

Following the procedure described in Example B-1 but using in place of methyl 2-chloro-5-(4-pyridinyl)nicotinate and 1,1-dimethylhydrazine or 1-methylhydrazine corresponding molar equivalent quantities of the appropriate methyl or other lower-alkyl 2-chloro-5-PY-nicotinate and 1-(lower-hydroxyalkyl)-hydrazine, it is contemplated that the 1,2-dihydro-3-oxo-5-PY-3H-pyrazolo[3,4-b]pyridine-1-(lower-alkanols) of Example B-20 through B-27 can be obtained.

B-20. 1,2-Dihydro-3-oxo-5-(3-pyridinyl)-3H-pyrazolo[3,4-b]pyridine-1-ethanol.

B-21. 1,2-Dihydro-3-oxo-5-(2-methyl-3-pyridinyl)-3H-pyrazolo[3,4-b]pyridine-1-ethanol.

B-22. 1,2-Dihydro-3-oxo-5-(5-methyl-3-pyridinyl)-3H-pyrazolo[3,4-b]pyridine-1-(n-propanol).

B-23. 1,2-Dihydro-3-oxo-5-(4-pyridinyl)-3H-pyrazolo[3,4-b]pyridine-1-(2-propanol).

B-24. 1,2-Dihydro-3-oxo-5-(3-ethyl-4-pyridinyl)-3H-pyrazolo[3,4-b]pyridine-1-(2-butanol).

B-25. 1,2-Dihydro-3-oxo-5-(2-methyl-4-pyridinyl)-3H-pyrazolo[3,4-b]pyridine-1-ethanol.

B-26. 1,2-Dihydro-3-oxo-5-(2,6-dimethyl-4-pyridinyl)-3H-pyrazolo[3,4-b]pyridine-1-ethanol.

B-27. 1,2-Dihydro-3-oxo-5-(4-pyridinyl)-3H-pyrazolo[3,4-b]pyridine-1-ethanol.

Following the procedure described in Example B-1 but using in place of methyl 2-chloro-5-(4-pyridinyl)nicotinate and 1,1-dimethylhydrazine or 1-methylhydrazine molar equivalent quantities of the appropriate methyl or other lower-alkyl 2-chloro-5-PY-6-(lower-alkyl)nicotinate and/or 1-R-hydrazine, respectively, it is contemplated that the corresponding 1,2-dihydro-1-R-5-PY-6-Q-1H-pyrazolo[3,4-b]pyridin-3-ones of Examples B-28 through B-41 can be obtained.

B-28. 1,2-Dihydro-1,6-dimethyl-5-(4-pyridinyl)-3H-pyrazolo[3,4-b]pyridin-3-one.

B-29. 6-Ethyl-1,2-dihydro-1-methyl-5-(4-pyridinyl)-3H-pyrazolo[3,4-b]pyridin-3-one.

B-30. 1,2-Dihydro-6-methyl-5-(4-pyridinyl)-3H-pyrazolo[3,4-b]pyridin-3-one.

B-31. 1-Ethyl-1,2-dihydro-6-methyl-5-(3-pyridinyl)-3H-pyrazolo[3,4-b]pyridin-3-one.

B-32. 1,2-Dihydro-6-methyl-3-oxo-5-(4-pyridinyl)-3H-pyrazolo[3,4-b]pyridine-1-ethanol.

B-33. 1,2-Dihydro-6-methyl-3-oxo-5-(4-pyridinyl)-3H-pyrazolo[3,4-b]pyridine-1-ethanol.

B-34. 1,2-Dihydro-1-methyl-6-n-propyl-5-(4-pyridinyl)-3H-pyrazolo[3,4-b]pyridin-3-one.

B-35. 1,2-Dihydro-6-isopropyl-5-(4-pyridinyl)-3H-pyrazolo[3,4-b]pyridin-3-one.

B-36. 6-n-Butyl-1,2-dihydro-1-methyl-5-(4-pyridinyl)-3H-pyrazolo[3,4-b]pyridin-3-one.

B-37. 1,2-Dihydro-6-isobutyl-3-oxo-5-(4-pyridinyl)-3H-pyrazolo[3,4-b]pyridine-1-ethanol.

B-38. 1,2-Dihydro-5-(4-pyridinyl)-6-tert.-butyl-3H-pyrazolo[3,4-b]pyridin-3-one.

B-39. 1,2-Dihydro-1-methyl-6-n-pentyl-5-(4-pyridinyl)-3H-pyrazolo[3,4-b]pyridin-3-one.

B-40. 1,6-Diethyl-1,2-dihydro-5-(2-methyl-4-pyridinyl)-3H-pyrazolo[3,4-b]pyridin-3-one.

B-41. 6-Ethyl-1,2-dihydro-3-oxo-5-(3-pyridinyl)-3H-pyrazolo[3,4-b]pyridine-1-ethanol.

Following the procedure described in Example B-20 but using in place of 1-(2-hydroxyethyl)hydrazine a corresponding molar equivalent quantity of 1-(2,3-dihydroxypropyl)hydrazine and either methyl 2-chloro-5-(4-pyridinyl)nicotinate or a corresponding molar equivalent quantity of the appropriate methyl or lower-alkyl 2-chloro-5-PY-6-Q-nicotinate, it is contemplated that there can be obtained the 1,2-dihydro-1-(2,3-dihydroxypropyl)-5-PY-6-Q-3H-pyrazolo[3,4-b]pyridin-3-ones of Examples B-42 through B-44.

B-42. 1,2-Dihydro-1-(2,3-dihydroxypropyl)-5-(4-pyridinyl)-1H-pyrazolo[3,4-b]pyridin-3-one.

B-43. 1,2-Dihydro-1-(2,3-dihydroxypropyl)-6-methyl-5-(4-pyridinyl)-1H-pyrazolo[3,4-b]pyridin-3-one.

B-44. 1,2-Dihydro-1-(2,3-dihydroxypropyl)-5-(3-pyridinyl)-1H-pyrazolo[3,4-b]pyridin-3-one.

C. 1-PY-2-(DIMETHYLAMINO)ETHENYL LOWER ALKYL KETONES

C-1. 1-(4-Pyridinyl)-2-(dimethylamino)ethenyl methyl ketone—A mixture containing 20 g. of (4-pyridinyl)-methyl methyl ketone [alternatively named 1-(4-pyridinyl)-2-propanone] and 30 cc. of hexamethylphosphoramide was diluted with 65 cc. of dimethylformamide dimethyl acetal and the resulting mixture was refluxed for 30 minutes. TLC analysis showed a single spot, thereby indicating completion of the reaction (in another run, the reaction appeared to be complete after 30 minutes at room temperature). The reaction mixture was evaporated under reduced pressure using a rotary vaporizer and a pressure of about 0.5 mm., thereby resulting in a crystalline residue weighing 24 g. The residue was decolorized using continuous column chromatography on alumina (about 150 g. of alumina in a 500 cc. a continuous separating funnel) using refluxing chloroform. After 1 and ½ hours, the extract was heated in vacuo to remove the chloroform, thereby leaving, as a light yellow crystalline material, 23.2 g. of 1-(4-pyridinyl)-2-(dimethylamino)ethenyl methyl ketone, alternatively named 3-dimethylamino-4-(4-pyridinyl)-3-buten-2-one.

The above preparation can be carried out using in place of hexamethylphosphoramide other solvents, e.g., dimethylformamide, acetonitrile or others noted above; however, hexamethylphosphoramide was conveniently used since (4-pyridinyl)methyl methyl ketone was conveniently prepared as a mixture together with hexamethylphosphoramide, as seen by the following preparation: To a stirred solution containing 70 cc. of freshly distilled diisopropylamine and 200 cc. of tetrahydrofuran at 0° C. under nitrogen was added dropwise over 20 minutes 210 cc. of 2.4 M n-butyllithium in n-hexane and the reaction mixture was stirred for about 35 minutes at about 0°-5° C. To the cold solution was added dropwise over a period of 10 minutes 90 cc. of dry hexamethylphosphoramide (no temperature change) and a resulting light yellow solution was stirred for 15 minutes. To the cold solution at 0° C. was added a solution of 50 cc. of 4-picoline in 150 cc. of dry tetrahydrofuran over a 15 minute period and stirring was continued for 30 minutes at 0° C. Next, a mixture containing 50 cc. of dry ethyl acetate and 150 cc. of tetrahydrofuran was added over a 15 minute period (temperature rose from 0° to about 6° C.) and the resulting mixture was stirred for 20 minutes at 0° C. The ice bath was then removed and stirring continued for another 90 minutes whereupon the temperature of the reaction mixture rose to about 25° C. The reaction mixture was then cooled in an ice bath and to it was added 60 cc. of acetic acid over a period of about 30 minutes. The tetrahydrofuran was distilled off using a rotary vaporizer in vacuo. The remaining mixture was diluted with 400 cc. of water and the aqueous mixture was extracted successively with two 250 cc. portions of isopropyl acetate and three 80 cc. portions of chloroform. The solvents were distilled off under reduced pressure to yield about 137 g. of mixture consisting primarily of the desired product and hexamethylphosphoramide. Another run using the same quantities was carried out as above except after the addition of 60 cc. of glacial acetic acid, the mixture was diluted with only 200 cc. of water, the phases were separated, and the aqueous phase was extracted with five 100 ml. portions of chloroform. The chloroform extract was washed with saline solution and the chloroform was distilled off in vacuo. The remaining mixture of the desired ketone and hexamethylphosphoramide was combined with the above 137 g. of the same mixture and the combined mixture was distilled under reduced pressure to yield the following fractions: I. 63 g., b.p. of 110°–112° C. at 4 mm.; II. 59 g. of pale yellow oil, b.p. 113°–115° C. at 3 mm.; and, III. 69 g. of pale yellow oil, b.p. 115°–118° C. at 2.5 mm. Examination of fraction III by NMR showed it to contain 2:3 mixture by weight of (4-pyridinyl)methyl methyl ketone and hexamethylphosphoramide.

Acid-addition salts of 1-(4-pyridinyl)-2-(dimethylamino)ethenyl methyl ketone are conveniently prepared by adding to a mixture of 5 g. of 1-(4-pyridinyl)-2-(dimethylamino)ethenyl methyl ketone in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt; e.g., dimethanesulfonate, sulfate, phosphate, respectively. Also, the acid-addition salt is conveniently prepared in aqueous solution by adding to water with stirring molar equivalent quantities each of 1-(4-pyridinyl)-2-(dimethylamino)ethenyl methyl ketone and the appropriate acid, e.g., lactic acid or hydrochloric acid, to prepare respectively the monolactate or monohydrochloride salt in aqueous solution.

C-2. 1-(4-Pyridinyl)-2-(dimethylamino)ethenyl ethyl ketone—A mixture containing 87.5 g. of (4-pyridinyl)methyl ethyl ketone [alternatively named 1-(4-pyridinyl)-2-butanone] and 160 cc. of hexamethylphosphoramide was diluted with 100 g. of dimethylformamide dimethyl acetal and the resulting mixture was stirred under nitrogen at room temperature for 45 minutes. The methanol formed by the reaction was distilled off in vacuo using a rotary evaporator and the remaining material was distilled under reduced pressure to yield two fractions, one boiling at 45°–80° C. at 0.5 mm, and the second at 90°–95° C. at 0.5 mm. After TLC analysis showed predominantly only a single spot for each fraction, the two fractions were combined (135 g.) and taken up in 600 cc of chloroform. The resulting solution was washed with two 300 cc. portions of water and the water was back extracted with three 100 cc. portions of chloroform. The combined chloroform solution was dried over anhydrous sodium sulfate and decolorized by running it through 300 cc. of alumina in a 500 cc. continuous extraction funnel followed by extraction with refluxing chloroform. The chloroform was distilled off in vacuo to yield a red oil which crystallized on standing overnight in an ice bath. The crystalline material was dissolved in carbon tetrachloride, cyclohexane was added and the mixture cooled to yield 64 g. of the resulting yellow crystalline product, 1-(4-pyridinyl)-2-(dimethylamino)ethenyl ethyl ketone. Another 11 g. of crystalline product was obtained by passing the mother liquor through the continuous extraction column and using refluxing chloroform as the solvent.

The above intermediate (4-pyridinyl)methyl ethyl ketone was obtained in a mixture with hexamethylphosphoramide as follows: To a mixture containing 200 cc. of tetrahydrofuran and 70 cc. of diisopropylamine under nitrogen at 0°–5° C. was added 210 cc. of 2.4 N n-butyllithium in n-hexane and the resulting mixture was stirred for 30 minutes. Next was added over a 10 minute period 90 cc. of hexamethylphosphoramide followed by stirring of the mixture for 15 minutes. Then was added over a 15 minute period a solution of 48 cc. of 4-picoline in 150 cc. of tetrahydrofuran followed by stirring for 30 minutes at about 0° C. the ice/acetone bath cooling the reaction mixture was replaced with a dry ice/acetone bath and to the reaction mixture was added over a 20 minute period a mixture of 75 cc. of ethyl propionate in an equal volume of tetrahydrofuran. The reaction mixture was then allowed to warm up to room temperature over a period of about 90 minutes and then was warmed at about 35° C. for 30 minutes. The mixture was next cooled in an ice/acetone bath and to it was added 60 cc. of glacial acetic acid over 30 minutes. The resulting pale yellow suspension was diluted with 200 cc. of water. The mixture was extracted with three 150 cc. portions of ethyl acetate and the ethyl acetate extract was back washed with saline solution. The extract was heated in vacuo to remove the ethyl acetate and the residue was taken up again with ethyl acetate. The solution was washed with water and then heated in vacuo to remove the ethyl acetate followed by heating the residue in vacuo at 50° C. for about 30 minutes to yield 100 g. of pale yellow oil. The pale yellow oil was combined with corresponding samples obtained from two additional runs and then distilled in vacuo to yield a 256 g. fraction, b.p. 85°–105° C. at 0.5–1.0 mm. The NMR of this fraction showed it to be a mixture of (4-pyridinyl)methyl ethyl ketone and hexamethylphosphoramide in a respective molar ratio of 1:1.55, that is, 35% or 0.35×256=90 g. of said ketone.

Following the procedure described in Example C-2 but using a molar equivalent quantity of the appropriate PY-methyl lower-alkyl ketone (II) in place of (4-pyridinyl)methyl ethyl ketone, it is contemplated that the corresponding 1-PY-2-(dimethylamino)ethenyl lower-alkyl ketones of Examples C-3 thru C-17 can be obtained.

C-3. 1-(3-Pyridinyl)-2-(dimethylamino)ethenyl methyl ketone using (3-pyridinyl)methyl methyl ketone.

C-4. 1-(4-Pyridinyl)-2-(dimethylamino)ethenyl n-propyl ketone using (4-pyridinyl)methyl n-propyl ketone.

C-5. 1-(4-Pyridinyl)-2-(dimethylamino)ethenyl isopropyl ketone using (4-pyridinyl)methyl isopropyl ketone.

C-6. 1-(4-Pyridinyl)-2-(dimethylamino)ethenyl n-butyl ketone using (4-pyridinyl)methyl n-butyl ketone.

C-7. 1-(4-Pyridinyl)-2-(dimethylamino)ethenyl isobutyl ketone using (4-pyridinyl)methyl isobutyl ketone.

C-8. 1-(4-Pyridinyl)-2-(dimethylamino)ethenyl tert.-butyl ketone using (4-pyridinyl)methyl tert.-butyl ketone.

C-9. 1-(4-Pyridinyl)-2-(dimethylamino)ethenyl n-pentyl ketone using (4-pyridinyl)methyl n-pentyl ketone.

C-10. 1-(2-Methyl-4-pyridinyl)-2-(dimethylamino)ethenyl ethyl ketone using (2-methyl-4-pyridinyl)methyl ethyl ketone.

C-11. 1-(3-Pyridinyl)-2-(dimethylamino)ethenyl ethyl ketone using (3-pyridinyl)methyl ethyl ketone.

D. 1,2-DIHYDRO-6-(LOWER-ALKYL)-2-OXO-5-PY-NICOTINONITRILES

D-1. 1,2-Dihydro-6-methyl-2-oxo-5-(4-pyridinyl)-nicotinonitrile, alternatively named 1,6-dihydro-2-methyl-6-oxo-[3,4'-bipyridine]-5-carbonitrile—To a mixture containing 23 g. of 1-(4-pyridinyl)-2-(dimethylamino)ethenyl methyl ketone and 11 g. of α-cyanoacetamide dissolved in 400 cc. of dimethylformamide was added with stirring 14 g. of sodium methoxide and the resulting reaction mixture was heated in an oil bath under gentle reflux for one hour. TLC analysis showed no starting material in the reaction mixture which was then concentrated in vacuo on a rotary vaporator to a volume of about 80 cc. The concentrate was treated with about 160 cc. of acetonitrile and the resulting mixture was stirred on a rotary vaporator with warming until homogenuous and then cooled. The crystalline product was collected, rinsed successively with acetonitrile and ether, and dried overnight at 55° C. to yield 28 g. of tan crystalline product, namely, sodium salt of 1,2-dihydro-6-methyl-2-oxo-5-(4-pyridinyl)-nicotinonitrile, the presence of cyano being confirmed by IR analysis. An 8 g. portion of said sodium salt was dissolved in 75 cc. of hot water, the aqueous solution treated with decolorizing charcoal filtered, the filtrate again treated with decolorizing charcoal and filtered, and the filtrate acidified with 6 N hydrochloric acid by dropwise addition to a pH of 3. The acidic mixture was diluted with ethanol and cooled. The crystalline product was collected, dried, recrystallized from dimethylformamide-water and dried to produce 3.75 g. of 1,2-dihydro-6-methyl-2-oxo-5-(4-pyridinyl)nicotinonitrile, m.p. 300° C.

Acid-addition salts of 1,2-dihydro-6-methyl-2-oxo-5-(4-pyridinyl)nicotinonitrile are conveniently prepared by adding to a mixture of 2 g. of 1,2-dihydro-6-methyl-2-oxo-5-(4-pyridinyl)nicotinonitrile in about 40 ml. of aqueous methanol the appropriate acid, e.g., methanesulfonic acid, concentrated sulfuric acid, concentrated phosphoric acid, to a small pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 1,2-dihydro-6-methyl-2-oxo-5-(4-pyridinyl)nicotinonitrile and the appropriate acid, e.g., lactic acid or hydrochloric acid, to prepare respectively the monolactate or monohydrochloride salt in aqueous solution.

D-2. 6-Ethyl-1,2-dihydro-2-oxo-5-(4-pyridinyl)-nicotinonitrile, alternatively named 2-ethyl-1,6-dihydro-6-oxo-[3,4'-bipyridine]-5-carbonitrile, m.p. >300° C., 11.6 g., was prepared following the procedure described above in Example D-1 using 20 g. of 1-(4-pyridinyl)-2-(dimethylamino)ethenyl ethyl ketone, 8.4 g. of α-cyanoacetamide, 16.2 g. of sodium methoxide and 250 cc. of dimethylacetamide (as solvent in place of dimethylformamide).

Following the procedure described in Example D-2 but using a molar equivalent quantity of the appropriate 1-PY-2-(dimethylamino)ethenyl lower-alkyl ketone in place of 1-(4-pyridinyl)-2-(dimethylamino)ethenyl ethyl ketone, it is contemplated that the corresponding 1,2-dihydro-2-oxo-5-PY-6-R-nicotinonitriles of Examples D-3 thru D-11 can be obtained.

D-3. 1,2-Dihydro-6-methyl-2-oxo-5-(3-pyridinyl)-nicotinonitrile, using 1-(3-pyridinyl)-2-(dimethylamino)-ethenyl methyl ketone.

D-4. 1,2-Dihydro-2-oxo-6-n-propyl-5-(4-pyridinyl)-nicotinonitrile, using 1-(4-pyridinyl)-2-(dimethylamino)ethenyl n-propyl ketone.

D-5. 1,2-Dihydro-6-isopropyl-2-oxo-5-(4-pyridinyl)-nicotinonitrile, using 1-(4-pyridinyl)-2-(dimethylamino)ethenyl isopropyl ketone.

D-6. 6-n-Butyl-1,2-dihydro-2-oxo-5-(4-pyridinyl)-nicotinonitrile, using 1-(4-pyridinyl)-2-(dimethylamino)ethenyl n-butyl ketone.

D-7. 1,2-Dihydro-6-isobutyl-2-oxo-5-(4-pyridinyl)-nicotinonitrile using 1-(4-pyridinyl)-2-(dimethylamino)ethenyl isobutyl ketone.

D-8. 1,2-Dihydro-2-oxo-5-(4-pyridinyl)-6-tert.-butyl-nicotinonitrile, using 1-(4-pyridinyl)-2-(dimethylamino)ethenyl tert.-butyl ketone.

D-9. 1,2-Dihydro-2-oxo-6-n-pentyl-5-(4-pyridinyl)-nicotinonitrile using 1-(4-pyridinyl)-2-(dimethylamino)ethenyl n-pentyl ketone.

D-10. 6-Ethyl-1,2-dihydro-5-(2-methyl-4-pyridinyl)-2-oxonicotinonitrile, using 1-(2-methyl-4-pyridinyl)-2-(dimethylamino)ethenyl ethyl ketone.

D-11. 6-Ethyl-1,2-dihydro-2-oxo-5-(3-pyridinyl)-nicotinonitrile, using 1-(3-pyridinyl)-2-(dimethylamino)ethenyl ethyl ketone.

E. 1,2-DIHYDRO-6(LOWER-ALKYL)-2-OXO-5-PY-NICOTINIC ACIDS

Following the procedure described in Example B-1 of U.S. Pat. No. 4,072,746 but using in place of 1,2-dihydro-2-oxo-5-(4-pyridinyl)nicotinitrile a molar equivalent quantity of the corresponding 1,2-dihydro-2-oxo-5-PY-6-(lower-alkyl)nicotinonitrile, it is contemplated that there can be obtained the 1,2-dihydro-2-oxo-5-PY-6-(lower-alkyl)nicotinic acids of Examples E-1 through E-11.

E-1. 1,2-Dihydro-6-methyl-2-oxo-5-(4-pyridinyl)-nicotinic acid.

E-2. 6-Ethyl-1,2-dihydro-2-oxo-5-(4-pyridinyl)nicotinic acid.

E-3. 1,2-Dihydro-6-methyl-2-oxo-5-(3-pyridinyl)-nicotinic acid.

E-4. 1,2-Dihydro-2-oxo-6-n-propyl-5-(4-pyridinyl)-nicotinic acid.

E-5. 1,2-Dihydro-2-oxo-6-isopropyl-5-(4-pyridinyl)-nicotinic acid.

E-6. 6-n-Butyl-1,2-dihydro-2-oxo-5-(4-pyridinyl)-nicotinic acid.

E-7. 1,2-Dihydro-6-isobutyl-2-oxo-5-(4-pyridinyl)-nicotinic acid.

E-8. 1,2-Dihydro-2-oxo-5-(4-pyridinyl)-6-tert.-butyl-nicotinic acid.

E-9. 1,2-Dihydro-2-oxo-6-n-pentyl-5-(4-pyridinyl)-nicotinic acid.

E-10. 6-Ethyl-1,2-dihydro-5-(2-methyl-4-pyridinyl)-2-oxonicotinic acid.

E-11. 6-Ethyl-1,2-dihydro-2-oxo-5-(3-pyridinyl)nicotinic acid.

The usefulness of the compounds of formula I or salt thereof as a cartiotonic agent is demonstrated by its effectiveness in standard pharmacological test procedures, for example, in causing a significant increase in the contractile force of the isolated cat atria and papillary muscle. A detailed description of this test procedure appears in U.S. Pat. No. 4,072,746, issued Feb. 7, 1980.

When tested by said isolated cat atria and papillary muscle procedure, the 1,2-dihydro-5-(pyridinyl)-3H-pyrazolo[3,4-b]pyridin-3-ones of formula I when tested at a dose of 100 µg./ml., were found to cause significant increase, that is, about 25% or greater in papillary muscle force and a significant increase, that is, about 25% or greater, in right atrial force, while causing a lower percentage increase (about one-half or less than the percentage increase in right atrial force or papillary muscle force) in right atrial rate. For example, when tested at 100 µg./ml. by this procedure, the 1,2-dihydro-1-methyl-5-(4-pyridinyl)-3H-pyrazolo[3,4-b]pyridin-3-one was found to cause respective percentages increases of 23%, 42% and 12% in papillary muscle force, right atrial force and right atrial rate. In contrast 1,2-dihydro-5-(4-pyridinyl)-3H-pyrazolo[3,4-b]pyridin-3-one when tested at 100 µg./ml. by this procedure was found to be essentially inactive that is, to cause respective percentage increases of only 6%, 14% and 10% in papillary muscle force, right atrial force and right atrial rate.

The present invention includes within its scope a cardiotonic composition for increasing cardiac contractility, said composition comprising a pharmaceutically-acceptable carrier and, as the active component thereof, the cardiotonic 1,2-dihydro-5-PY-6-Q-3H-pyrazolo[3,4-b]pyridin-3-one of formula I or pharmaceutically-acceptable acid-addition salt thereof. The invention also includes within its scope the method for increasing cardiac contractility in a patient requiring such treatment which comprises administering to such patient an effective amount of cardiotonic 1,2-dihydro-5-PY-6-Q-3H-pyrazolo[3,4-b]pyridin-3-one of formula I or pharmaceutically acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, perserving, wetting, emulsifying and dispersing agents.

They can be sterilized, for example by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentages of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. 1,2-Dihydro-1-R-5-PY-6-Q-3H-pyrazolo[3,4-b]pyridin-3-one having the formula

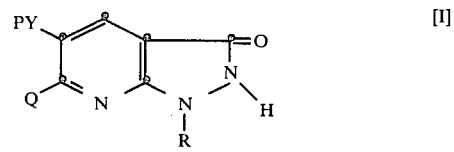

where R is lower-alkyl, lower-hydroxyalkyl having from two to six carbon atoms, 2,3-dihydroxypropyl or lower-alkoxyalkyl having from three to six carbon atoms, Q is hydrogen or lower-alkyl, PY is 4- or 3-pyridinyl or 4- or 3-pyridinyl having one or two lower-alkyl substituents, and where lower-alkyl, all occurrences not specifically defined above, contains from one to six carbon atoms, or pharmaceutically-acceptable acid-addition salt thereof.

2. A compound according to claim 1 where R is methyl or ethyl.

3. A compound according to claim 1 where R is 2-hydroxyethyl.

4. A compound according to claim 1 where Q is hydrogen.

5. A compound according to claim 1 where Q is methyl or ethyl.

6. 1,2-Dihydro-1-methyl-5-(4-pyridinyl)-3H-pyrazolo[3,4-b]pyridin-3-one or pharmaceutically-acceptable acid-addition salt thereof.

7. 1,2-Dihydro-3-oxo-5-(4-pyridinyl)-3H-pyrazolo[3,4-b]pyridine-1-ethanol or pharmaceutically-acceptable acid-addition salt thereof.

8. A cardiotonic composition for increasing cardiac contractility, said composition comprising a pharmaceutically-acceptable inert carrier and, as the active component thereof, an effective amount for increasing cardiac contractility of the cardiotonic 1,2-dihydro-1-R-5-PY-6-Q-3H-pyrazolo[3,4-b]pyridin-3-one or pharmaceutically-acceptable acid-addition salt thereof where R is lower-alkyl, lower-hydroxyalkyl having from two to six carbon atoms, 2,3-dihydroxypropyl or lower-alkoxyalkyl having from three to six carbon atoms, Q is hydrogen or lower-alkyl, PY is 4- or 3-pyridinyl or 4- or 3-pyridinyl having one or two lower-alkyl substituents, and where lower-alkyl, all occurrences not specifically defined above, contains from one to six carbon atoms.

9. The method for increasing cardiac contractility in a patient requiring such treatment which comprises administering orally or parenterally in a solid or liquid dosage form to such patient an effective amount for increasing cardiac contractility of the cardiotonic 1,2-dihydro-1-R-5-PY-5-Q-3H-pyrazolo[3,4-b]pyridin-3-one or pharmaceutically-acceptable acid-addition salt thereof where R is lower-alkyl, lower-hydroxyalkyl having from two or six carbon atoms, 2,3-dihydroxypropyl or lower-alkoxyalkyl having from three to six carbon atoms, Q is hydrogen or lower-alkyl, PY is 4- or 3-pyridinyl or 4- or 3-pyridinyl having one or two lower-alkyl substituents, and where lower-alkyl, all occurrences not specifically defined above, contains from one to six carbon atoms.

10. A composition according to claim 8 where R is methyl or ethyl.

11. A composition according to claim 8 where R is 2-hydroxyethyl.

12. A composition according to claim 8 where Q is hydrogen.

13. A composition according to claim 8 where Q is methyl or ethyl.

* * * * *

UNITED STATES PATENT AND TRADEMARK OFFICE
CERTIFICATE OF CORRECTION

PATENT NO. : 4,265,895
DATED : May 5, 1981
INVENTOR(S) : G.Y. Lesher and M.D. Gruett It is certified that error appears in the above-identified patent and that said Letters Patent are hereby corrected as shown below:

Column 18, Claim 9, line 1, "or" should read -- to --.

Signed and Sealed this

Twenty-ninth Day of September 1981

[SEAL]

Attest:

GERALD J. MOSSINGHOFF

Attesting Officer

Commissioner of Patents and Trademarks